United States Patent [19]

Moriuchi et al.

[11] 4,358,376
[45] Nov. 9, 1982

[54] APPARATUS FOR DETOXIFYING BODY FLUID

[75] Inventors: Yousuke Moriuchi, Fujinomiya; Atsushi Shimizu, Tokyo, both of Japan

[73] Assignee: Terumo Corporation, Tokyo, Japan

[21] Appl. No.: 200,915

[22] Filed: Oct. 27, 1980

[30] Foreign Application Priority Data

Oct. 29, 1979 [JP] Japan .................................. 54-139465
Oct. 29, 1979 [JP] Japan .................................. 54-139467

[51] Int. Cl.³ ............................................. B01D 15/00
[52] U.S. Cl. ..................................... 210/282; 210/927
[58] Field of Search ............... 210/694, 807, 266, 287, 210/446, 927, 282; 252/444

[56] References Cited

U.S. PATENT DOCUMENTS

| 3,725,113 | 4/1973 | Chang . |
| 3,770,625 | 11/1973 | Wallis et al. ........................ 210/694 |
| 3,888,250 | 6/1975 | Hill . |
| 4,169,051 | 9/1979 | Satoh et al. ........................... 210/694 |
| 4,250,141 | 2/1981 | Lehmann et al. ................... 210/927 |

OTHER PUBLICATIONS

Takahira et al. "Development of an Artificial Kidney Using Encapsulated Adsorbents, I, The Physicochemical Properties of Activated Charcoals from Different Origins as an Adsorbent", Yakugaku Zasshi (Magazine of Pharmacy), vol. 98, pp. 1480–1485 (11/78).

Primary Examiner—Ivars C. Cintins
Attorney, Agent, or Firm—Frishauf, Holtz, Goodman & Woodward

[57] ABSTRACT

An apparatus for detoxifying body fluid has a columnar hollow container with an inlet and an outlet for body fluid. This container is filled with non-coated petroleum pitch activated carbon particles which have been washed by ultrasonic waves to a degree that the number of carbon dust fine particles released in a physiologically acceptable solution is less than 100 particles/ml for particles of more than 2μ diameter and less than 10 particles/ml for particles of more than 5μ diameter.

9 Claims, 10 Drawing Figures

APPARATUS FOR DETOXIFYING BODY FLUID

The present invention relates to an apparatus for detoxifying a body fluid and, more particularly, to a body fluid detoxifying apparatus utilizing activated carbon.

A body fluid detoxifying apparatus conventionally used as an auxiliary device for artificial livers and kidneys comprises a column filled with coconut husk activated carbon, petroleum pitch activated carbon or the like. Many fine particles (carbon dust) are attached to activated carbon. When the body fluid is made to pass through the column filled with such activated carbon, the fine particles are released into the body fluid and cause ill effects in human body. These fine particles can also cause attachment of blood cells or the thrombus formation. In order to prevent release of carbon dust, it is general practice to coat the surface of the activated carbon with a water insoluble, biocompatible polymer such as collodion, poly(hydroxyethyl methacrylate), acetylcellulose, cellulose derivatives, and hydrogel.

However, coating of activated carbon with such a polymer results in decrease of its adsorption ability. Due to this, a large amount of activated carbon must be used to obtain a desired amount of adsorption, requiring a large apparatus. This in turn results in a larger amount of priming for the apparatus and a large load on the patient during extracorporeal circulation. In addition, the coated film of activated carbon contains some organic solvent which was used to dissolve the polymer for coating. Such a residual organic solvent or coating material may be eluted during autoclave sterilization and long term storage, which may cause many problems on the human body.

The use of a tackifier has also been proposed for adhering non-coated coconut husk activated carbon to a tape for preventing release of carbon dust fine particles. Although this method does not result in decrease of adsorption ability, an apparatus which adopts this type of activated carbon is complex in structure and expensive. Furthermore, when such activated carbon is brought into contact with a body fluid such as blood, the tackifier or other impurities may be eluted.

It is, therefore, an object of the present invention to provide an apparatus for detoxifying a body fluid which utilizes the adsorption ability of pure activated carbon and which does not adversely affect body fluids.

It is another object of the present invention to provide an apparatus for detoxifying a body fluid which uses non-coated activated carbon.

According to the present invention, there is provided an apparatus for detoxifying a body fluid comprising a columnar hollow container having an inlet and an outlet for body fluid; and non-coated petroleum pitch activated carbon particles filled in said container, said activated carbon particles having been washed in a phsiologically acceptable cleaning solution with ultrasonic waves until the number of carbon dust fine particles released in the cleaning solution is less than 100 particles/ml for particles of more than $2\mu$ particle size and less than 10 particles/ml for particles of more than $5\mu$ particle size.

Generally, filtering materials having pores sufficiently small for supporting activated carbon are disposed at the inlet side and the outlet side of the container.

Activated carbon generally has a particle diameter of 0.1 to 1 mm and the filtering materials have pores 200 to $250\mu$ in diameter.

The container, in general, preferably has a capacity of 50 to 600 cc, and it is preferable that activated carbon be filled in the container to the maximum density.

Within the container is also filled a physiologically acceptable liquid, e.g., water, a physiological saline solution, an aqueous dextran solution or the like. This filling solution preferably contains 50 to 5,000 units of heparin per gram of activated carbon.

This invention can be more fully understood from the following detailed description when taken in conjunction with the accompanying drawings, in which.

The present invention will now be described in more detail with reference to the accompanying drawings.

Figure 1:
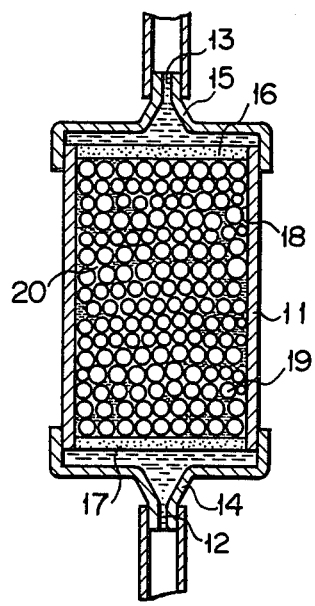
FIG. 1 is a schematic sectional view of a blood detoxifying apparatus in accordance with one embodiment of the present invention.

FIG. 1 shows a blood detoxifying apparatus in accordance with one embodiment of the present invention. This apparatus includes a columnar container 11 with covers 14 and 15 having an inlet 12 and an outlet 13 at the open ends, respectively. At these open ends are disposed filters 16 and 17 capable of supporting activated carbon to be described hereinafter. The filters have pores small enough to prevent the activated carbon from flowing out, and these filters define a space 18 inside the container. This space 18 generally has a capacity of 50 to 600 cc, and the pores of the filters are 200 to $250\mu$ in diameter.

Petroleum pitch activated carbon particles 19 are filled in the space 18 preferably to the maximum density so as to prevent the collisions resulting in fine particles. Petroleum pitch activated carbon is generally obtained by fusion formation (granulation) of petroleum pitch. It is composed of spherical particles about 0.1 to 1 mm in particle size. Petroleum pitch activated carbon is preferable to coconut husk activated carbon and other kinds of activated carbon since it shows high adsorption ability for low molecular materials as well as for medium and high molecular materials, its hardness is high, its surfaces are smooth, and release of carbon fine particles is relatively small when brought into contact with blood.

Such petroleum pitch activated carbon is washed or cleaned well before it is used in the body fluid detoxifying apparatus of the present invention. According to the present invention, the cleaning is performed by ultrasonic cleaning method. This cleaning is performed until the number of carbon dust fine particles released in a physiologically acceptable cleaning solution such as sterile water, a physiological saline solution, or an aqueous dextran solution is less than 100 particles/ml for particles over $2\mu$ in particle size, and less than 10 particles/ml for particles over $5\mu$ in particle size. (Measurements of carbon dust fine particles are performed using the Coulter counter). When the carbon dust fine particles released in the cleaning solution are outside the above range, the activated carbon is regarded as being insufficiently washed, and as such cannot be considered safe with respect to the attachment of blood cells or the thrombus formation.

Figure 2:
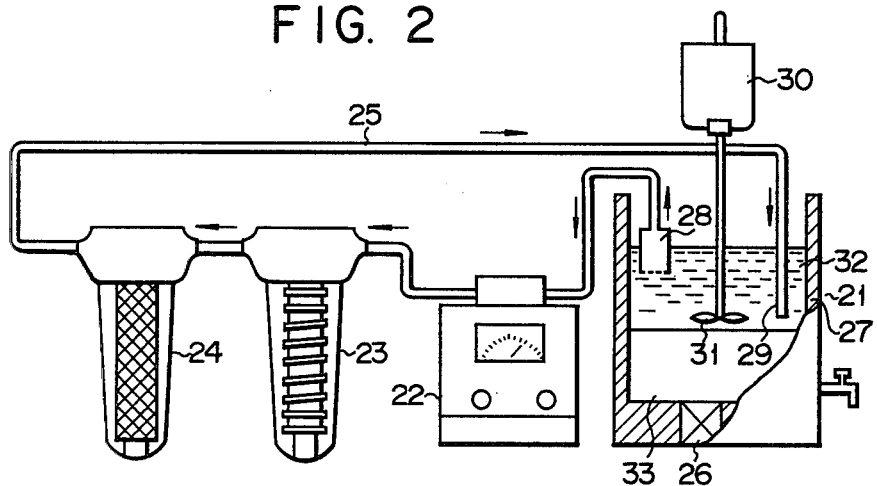
FIG. 2 is a schematic view illustrating a cleaning device for petroleum pitch activated carbon used in the invention.

The cleaning of activated carbon with ultrasonic means is preferably performed using a cleaning device as shown in FIG. 2. The cleaning device has an ultrasonic cleaning device 21, a circulating pump 22, and first and second filtering devices 23 and 24, and it defines a cleaning solution circulating channel 25 between these parts. The ultrasonic cleaning device 21 has a bath tank 27 with an ultrasonic oscillator 26, a solution inlet 28 and a solution outlet 29 with a mesh disposed inside the bath tank 27 for the cleaning solution circulating channel 25, and an agitating propeller 31 driven by a motor 30. The bath tank 27 is filled with a physiologically acceptable cleaning solution 32 such as a physiological saline solution, sterile water, or an aqueous dextran solution into which is poured petroleum pitch activated carbon 33. The cleaning solution preferably contains dextran. The first filtering device 23 has a cartridge filter of $5\mu$ pore diameter and the second filtering device 24 has a cartridge filter of $1\mu$ pore diameter. Such filters of about 0.2 to $5\mu$ pore diameter may be used in two or three stages.

Using this cleaning device, the ultrasonic oscillator 26 is operated to separate and remove the fine particles and impurities adhering to the petroleum pitch activated carbon 33, and the propeller 31 is turned for agitation to facilitate the cleaning effects. The cleaning solution 32 containing the fine particles and impurities passes, by the action of the pump 22, through the solution inlet 28 to the first and second filtering devices 23 and 24. Fine particles of over $5\mu$ particle size are removed in the first filtering device 23, and fine particles and impurities of 1 to $5\mu$ particle size are removed in the second filtering device 24. The cleaning solution 32 thus cleaned is brought back to the bath tank 27 through the solution outlet 29. The petroleum pitch activated carbon 13 is thus sufficiently cleaned while circulating the cleaning solution 32 in this manner.

According to this cleaning method, the cleaning conditions depend on the quality of the activated carbon used and the characteristics and scale of the device. Cleaning is generally performed at a flow rate of 0.5 to 5.0 l/min for 1 to 4 hours to clean 1 kg of petroleum pitch activated carbon until the number of released carbon dust fine particles of more than $2\mu$ particle size in the cleaning solution is less than 100 particles/ml and the number of particles of more than $5\mu$ particle size is less than 10 particles/ml.

The petroleum pitch activated carbon 33 thus sufficiently cleaned with ultrasonic waves undergoes several decantation cleanings and is thereafter filled into the container 11 as it is (i.e., without being coated with some substance) as shown in FIG. 1.

In order to avoid drying of activated carbon it is, generally, immersed in a physiologically acceptable solution 20 in the container 11 as shown in FIG. 1. This filling solution includes water, physiological saline water and the like. This filling solution may be the cleaning solution obtained from the final step of the ultrasonic cleaning process as described above.

The present inventors have further found that the addition of 50 to 5,000 units of heparin (according to the international unit) per gram of activated carbon to the filling solution 20 further prohibits the coagulation of blood passing through the body fluid detoxifying apparatus. When 50 to 5,000 units, preferably 200 to 2,000 units, of heparin per gram of activated carbon is added to the filling solution 20 and contacted with the activated carbon for at least about 6 hours, most of heparin flows away after cleaning the apparatus before use with a physiological solution or the like, but part of it remains in the pores or on the surface of the activated carbon for a long period of time. The residual heparin prevents decrease of the adsorption ability of the activated carbon, coagulation of blood, and damage to platelets. The heparin preferably has a molecular weight of about 5,000 to 25,000.

After filling the container 11 with the activated carbon and the filling solution, autoclave sterilization is performed with the inlet 12 and outlet 13 sealed with an expandable cap formed of, for example, a silicone resin to provide blood detoxifying apparatus for artificial livers and kidneys. The sterilization can be performed with the apparatus sealed in a bag.

This detoxifying apparatus functions to adsorb organic materials and toxious materials of middle molecules contained in blood, such as creatinine, inulin, pesticides, and sleeping drugs, for removing them. Since the fine particles and impurities have been removed from the petroleum pitch activated carbon, blood cells such as platelets do not substantially become attached to the activated carbon, the influx of the fine particles into the human body and formation of thrombi may be prevented, and the biocompatibility of the apparatus may be made equivalent to a conventional device using coated activated carbon. Furthermore, since activated carbon is not coated in the present invention, the adsorption ability is high, and organic solvent residues and elution of the coating material involved in coating the activated carbon are eliminated.

The body fluid detoxifying apparatus of the present invention may be applied not only to blood cleaning, but also to cleaning of plasma separated in plasma-separating devices.

The present invention will now be described by way of its examples.

EXAMPLE 1

For the cleaning device shown in FIG. 2, a "solid state 600" manufactured by Ultrasonic Industry K.K. was used as the ultrasonic cleaning device, and cartridge filters ($1\mu$ and $5\mu$) manufactured by Tateishi Roka K.K. were used as the filtering devices. Into this ultrasonic cleaning device was poured 1 kg of petroleum pitch activated carbon having a diameter of 0.4–1 mm (BAC-MU-ND, trade mark of Kureha Kagaku K.K.), and sterilized physiological saline solution was added. Cleaning was continuously performed at a flow rate of 3 l/min for 3 hours. After this cleaning operation, the cartridge filters were inspected. They were found to be darkened by released fine particles, and it was thus confirmed that fine particles were trapped here. The number of fine particles in the physiological saline solution flowing out of the solution outlet was measured with a Coulter counter (ZB type, manufactured by Coulter Electronics Inc). The number of fine particles was found to be less than 100 particles/ml for particles of more than $2\mu$ particle size, and was 0 particle/ml for those of more than $5\mu$ particle size. The cleaing solution was found to be clean.

Figure 3:
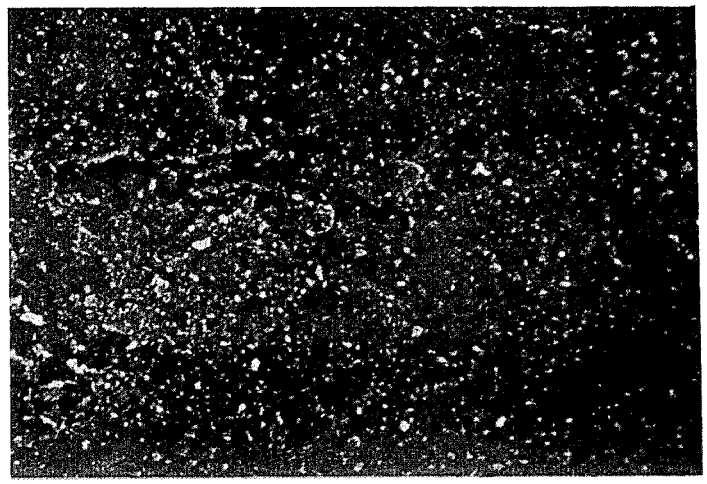
FIG. 3 is a photograph, as taken by a scanning electron microscope, of the petroleum pitch activated carbon before cleaning.
Figure 4:
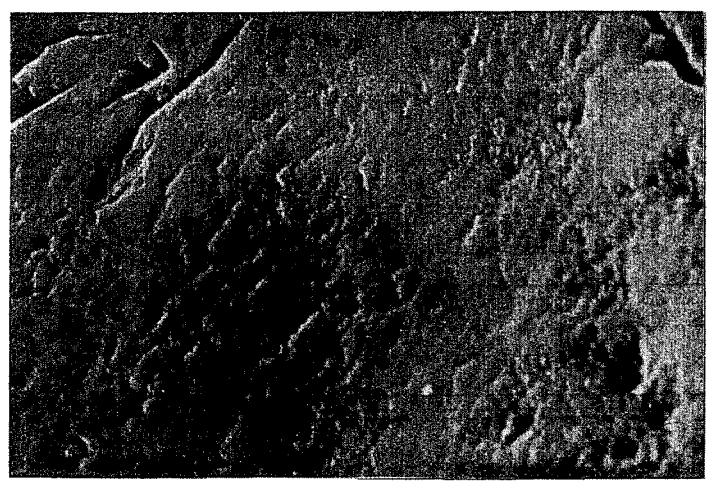
FIG. 4 is a photograph, as taken by a scanning electron microscope, of the petroleum pitch activated carbon after cleaning.

The surface of the activated carbon before and after cleaning were examined with a scanning electron microscope. Many fine particles were observed as shown in FIG. 3 before cleaning, but fine particles were not observed as shown in FIG. 4 after cleaning. It was thus confirmed that cleaning was effected to a satisfactory degree.

The petroleum pitch activated carbon cleaned in this manner was filled in an amount of 100 g into a column, and autoclave sterilization was performed with the inlet and the outlet sealed with silicone caps. Thereafter, a physiological saline solution filtered twice with a microporous membrane filter ($0.22\mu$) was made to pass at a flow rate of 200 ml/min. The number of fine particles remaining in the cleaned physiological saline solution after 5 minutes was measured by the Coulter counter. The results are shown in Table 1.

AV shunts were prepared in a carotid artery and jugular vein of a mongrel dog of 24 to 28 kg weight to heparinize the whole body and form a blood circulating circuit for an artificial kidney. The above-mentioned column was connected to this circuit to conduct an extracorporeal circulation experiment.

Figure 5:
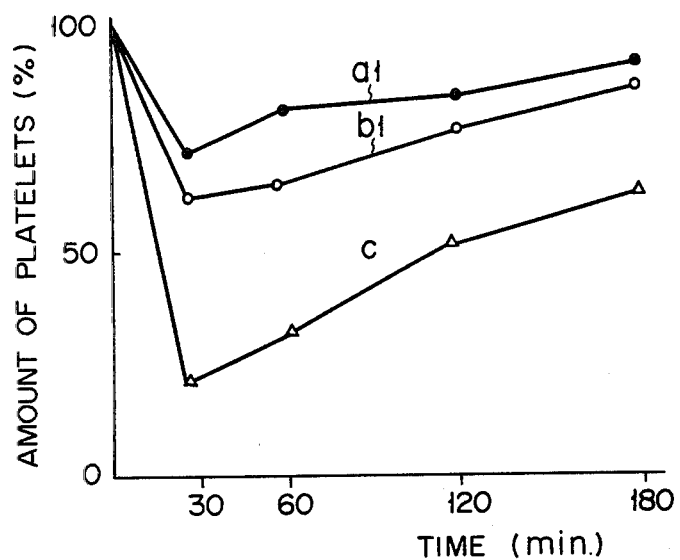
FIGS. 5 through 10 are graphs for showing the characteristics of the detoxifying apparatus of the present invention.

The fluctuations in the number of platelets during the extracorporeal circulation experiment were measured, and the results are shown by curve a1 in the graph presented in FIG. 5. Petroleum pitch activated carbon sterilized with an autoclave was filled into the abovementioned column in an amount of 100 g, and a solution of 20 mg/dl of vitamin B12 was made to pass at a flow rate of 200 ml/min with a single path. The fluctuations in the clearance KT during this process were measured, and the results are shown by a curve a2 in the graph presented in FIG. 6. The clearance KT may be defined by the following equation:

$$KT = \frac{Ci - CO}{Ci} \times QB$$

wherein:
KT: clearance (ml/min)
Ci: concentration of impurities at column inlet (mg %)
CO: concentration of impurities at column outlet (mg %)
QB: flow rate of solution (ml/min)

COMPARATIVE EXAMPLE 1

Poly(hydroxyethyl methacrylate) was added in an amount of 15 g as a coating material to 2 liters of ethanol. After heating the solution for dissolving the coating material, petroleum pitch activated carbon was added in an amount of 1 kg, and the ethanol was evaporated in warm air. After the liquid portion evaporated, the solid material was left in an oven kept at 90° C. for two days to prepare coated petroleum pitch activated carbon.

The activated carbon thus prepared was filled in an amount of 100 g into a column and sterilized with an autoclave in the same manner as in Example 1. Thereafter, a physiological saline solution was made to pass through it, and the fine particles in the solution were measured. The results are shown in Table 1. Similar experiments were conducted in which petroleum pitch activated carbon prepared in the same manner as in Example 1 was used, but it was not cleaned. The results are also shown in Table 1.

Extracorporeal circulation experiments were conducted in the same manner as in Example 1 using a column filled with coated petroleum pitch activated carbon and a column filled with uncleaned petroleum pitch activated carbon. The results are shown by a curve b1 (for coated activated carbon) and a curve c (for uncleaned activated carbon) in FIG. 5. The fluctuations in the clearance were measured with the coated activated carbon under the same conditions as in Example 1, and the results are shown by a curve b2 in FIG. 6.

TABLE 1

|  |  | Particle size | |
| --- | --- | --- | --- |
|  |  | More than $2\mu$ | More than $5\mu$ |
| Example | Cleaned activated carbon | 85 | 0 |
| Comparative Examples | Coated activated carbon | 72 | 0 |
|  | Uncleaned activated carbon | 2625 | 253 |

It is seen from Table 1 and FIG. 5 that, with the uncoated petroleum pitch activated carbon of the present invention, the fine particles are not released, the reduction in the number of platelets is small, and the biocompatibility is as good as in the case of conventional coated activated carbon.

Figure 6:
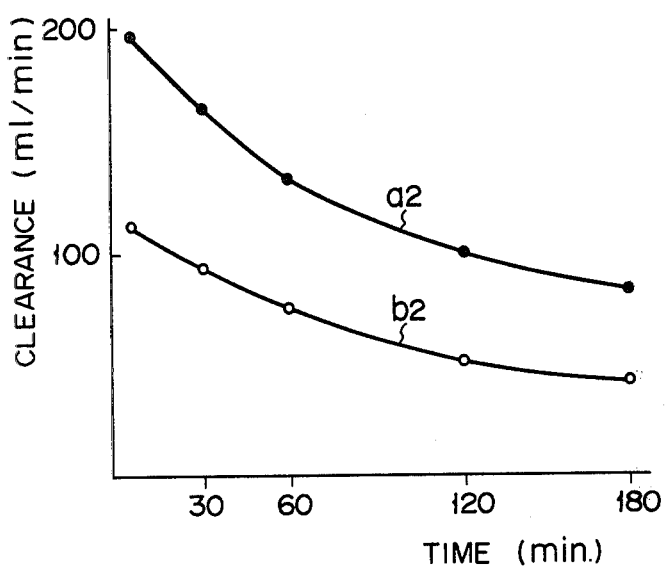

It is further seen from FIG. 6 that, with the petroleum pitch activated carbon of the present invention, the clearance may be kept higher and the adsorption ability may be improved to twice the level obtained with the coated activated carbon.

EXAMPLE 2

Petroleum pitch activated carbon (BAC-MU-ND, manufactured by Kureha Kagaku K.K.) sufficiently cleaned by the method of Example 1 was mixed in an amount of 100 g with 200 ml of a physiological saline solution containing 250 units/ml of heparin (average molecular weight: 15,000). The ratio of heparin to activated carbon was 500 units/g. The mixture was filled in a columnar container of 56 mm diameter and 81 mm height, and the container was sealed to provide an apparatus as shown in FIG. 1. The apparatus (DHP column) was sterilized in an autoclave. Physiological saline solution was made to pass through the column at a flow rate of 100 ml/min in an amount of 2 liters for cleaning the column as a preprocessing. After leaving it to stand for 30 minutes, physiological saline solution was made to pass through the column at a flow rate of 200 ml/min in an amount of 2 liters. The heparin amounts in the solutions flowing out in both cases of the physiological saline solutions were determined with the toluidine blue method. The results are shown in FIG. 7.

Figure 7:
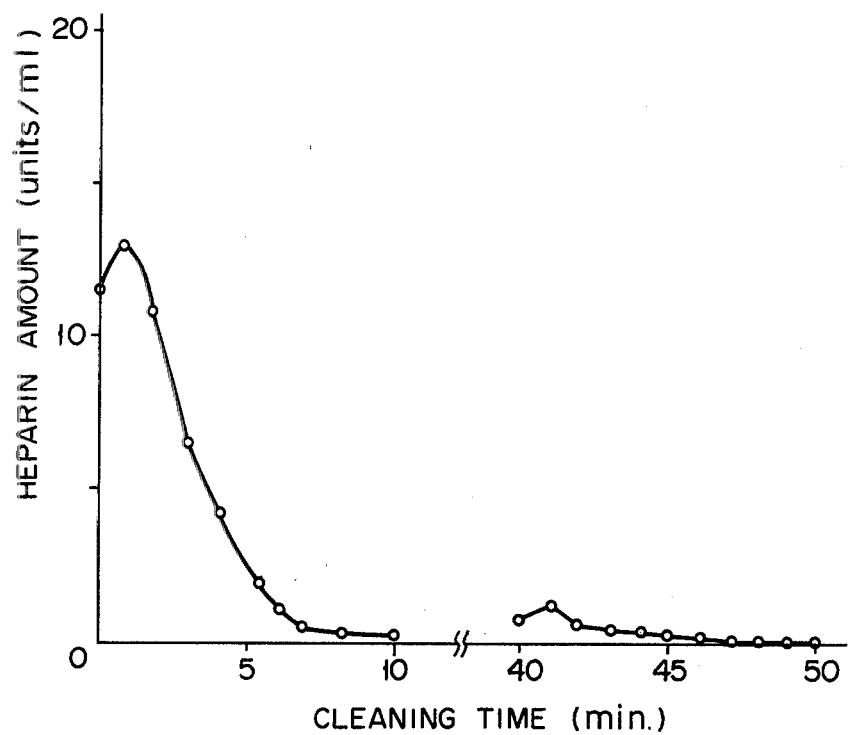

It may be seen from FIG. 7 that, although most of the heparin inside the columnar container is removed by the initial preprocessing of cleaning, part of it remains at the surface and in micropores and the like of the activated carbon, and this residual heparin provides local anticoagulant effects which presented excellent results, such as those obtained in the examples to follow.

EXAMPLE 3

A DHP column was prepared in a similar manner as in Example 2 except that the diameter and height of the container in Example 2 were changed to 20 mm and 30 mm, respectively, and in this column were filled 5 g of activated carbon and 10 ml of physiological saline solution containing 250 units/ml of heparin (heparin/activated carbon=500 units/g).

EXAMPLE 4

A DHP column was prepared in a similar manner as in Example 3, except that the amount of heparin in the physiological saline solution was 1,000 units/ml and the heparin per gram of activated carbon was 2,000 units/g.

COMPARATIVE EXAMPLE 2

The petroleum pitch activated carbon of Example 2 was mixed without cleaning with physiological saline solution in a ratio of 1 g of activated carbon to 2 ml of physiological saline solution, and the mixture was filled and sealed in the containers obtained in Examples 2 and 3, respectively. The amounts of the activated carbon and physiological saline solution in the containers were the same as above.

COMPARATIVE EXAMPLE 3

The petroleum pitch activated carbon of Example 1 in an amount of 1 kg was well washed and placed in an oven at 120° C. for about 24 hours for drying. Ethanol anhydride in an amount of 2 liters was heated to 80° C., and 15 g of poly (hydroxyethyl methacrylate) was added for dissolving it. The solution was then moved to a drying vat. After adding 1 kg of dried activated carbon to this, the ethanol was rapidly evaporated with heated air. The dried materials were further left to stand in an oven at 90° C. for 72 hours to provide activated carbon with an anticoagulant coating of about $1\mu$ thickness on the surface.

Using the resultant coated activated carbon, DHP columns of two different sizes were prepared in the same manner as in Comparative Example 2. The amounts of the activated carbon and the physiological saline solution were the same as described above.

EXPERIMENT 1

Extracorporeal circulation experiments were conducted with European rabbits for comparing anticoagulant properties and damage to the platelets with the DHP columns of Examples 3 and 4 and the small DHP columns of Comparative Examples 2 and 3.

Blood was circulated from the carotid artery of an European rabbit, through a pump to the DHP column disposed inside a thermostat at 37° C., to an air chamber, and into the jugular vein of the rabbit, in the order named. Each DHP column was sterilized in advance in an autoclave and was cleaned with 100 ml of physiological saline solution at a rate of 100 ml/min for preprocessing to perform the extracorporeal circulation. The circulation was performed at a rate of 20 ml blood/min for 2 hours. Before the circulation, 150 units/kg of heparin was gently dosed as in the general case, and heparin was not dosed thereafter.

Figure 8:
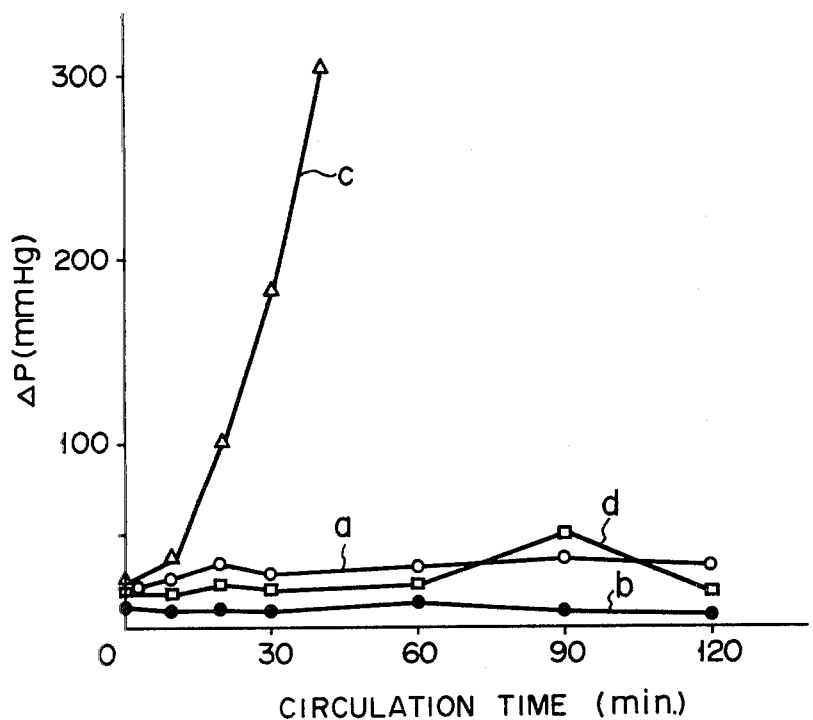
Figure 9:
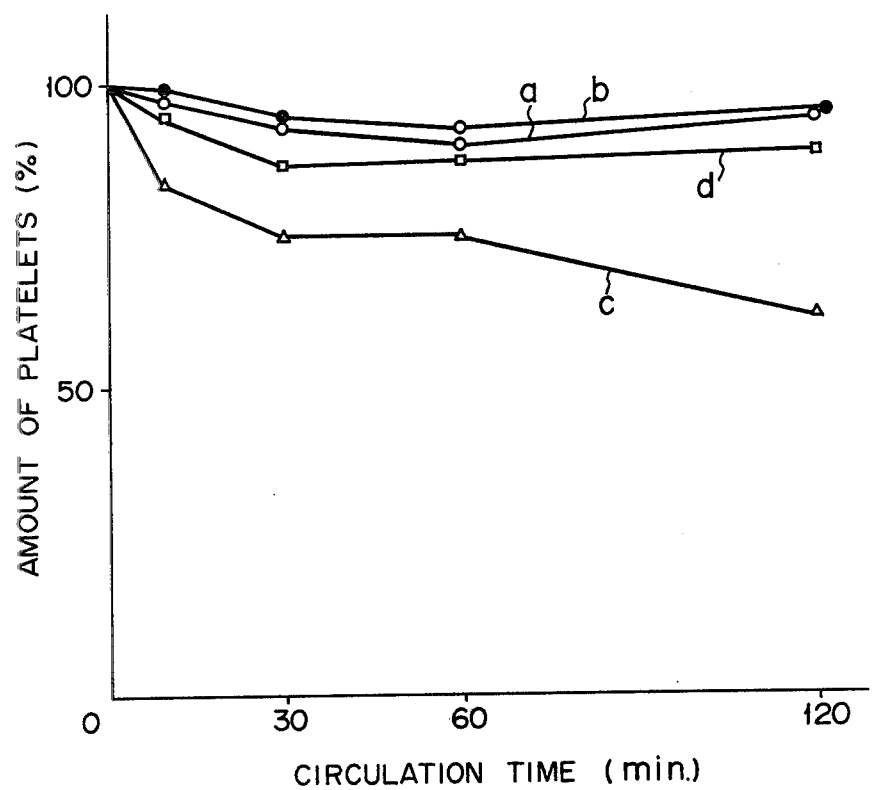

Performing the extracorporeal circulation in this manner, the rate of change of the pressure difference ($\Delta P$) with time at the inlet and outlet of the DHP column, ahd the percentage rate of change (based on the initial value) of the amount of platelets per unit were measured. The results are shown in FIGS. 8 and 9, respectively. In both of these figures, curves a, b, c and d indicate the results for Examples 3 and 4, and Comparative Examples 2 and 3, respectively.

It is seen from the results shown in FIG. 8 that $\Delta P$ increased with time in the case of Comparative Example 2 (curve c), coagulation occurred within the column and smooth flow of blood was prevented. The column was examined after the circulation, and a large number of thrombi were found.

To the contrary, in the cases of Examples 3 and 4 (curves a and b) as in the case of Comparative Example 3 (curve d), $\Delta P$ did not increase much and thrombi were not observed.

It is seen from the results shown in FIG. 9 that the rate of change in the amount of platelets was approximately equal in the cases of Examples 3 and 4 (curves a and b) and Comparative Example 3 (curve d), but it decreased to about 60% after circulation in the case of Comparative Example 2 (curve c).

EXPERIMENT 2

For comparison of adsorption ability of the DHP column prepared in Example 2 and the large DHP columns prepared in Comparative Examples 2 and 3, the change in clearance with time was measured taking creatinine, vitamin B12 and inulin as reference materials. Physiological saline solution containing 10 ml each of creatinine, vitamin B12 and inulin was filled in the tank, and to this were connected a heat exchanger, a blood pump, a bubble trap and the DHP column in the order named to form a single path channel. The DHP was used after being sterilized in an autoclave and cleaned with 2 liters of physiological saline solution at a rate of 100 ml/min.

The clearances of the solute reference materials were measured in the same manner as in Example 1.

Figure 10:
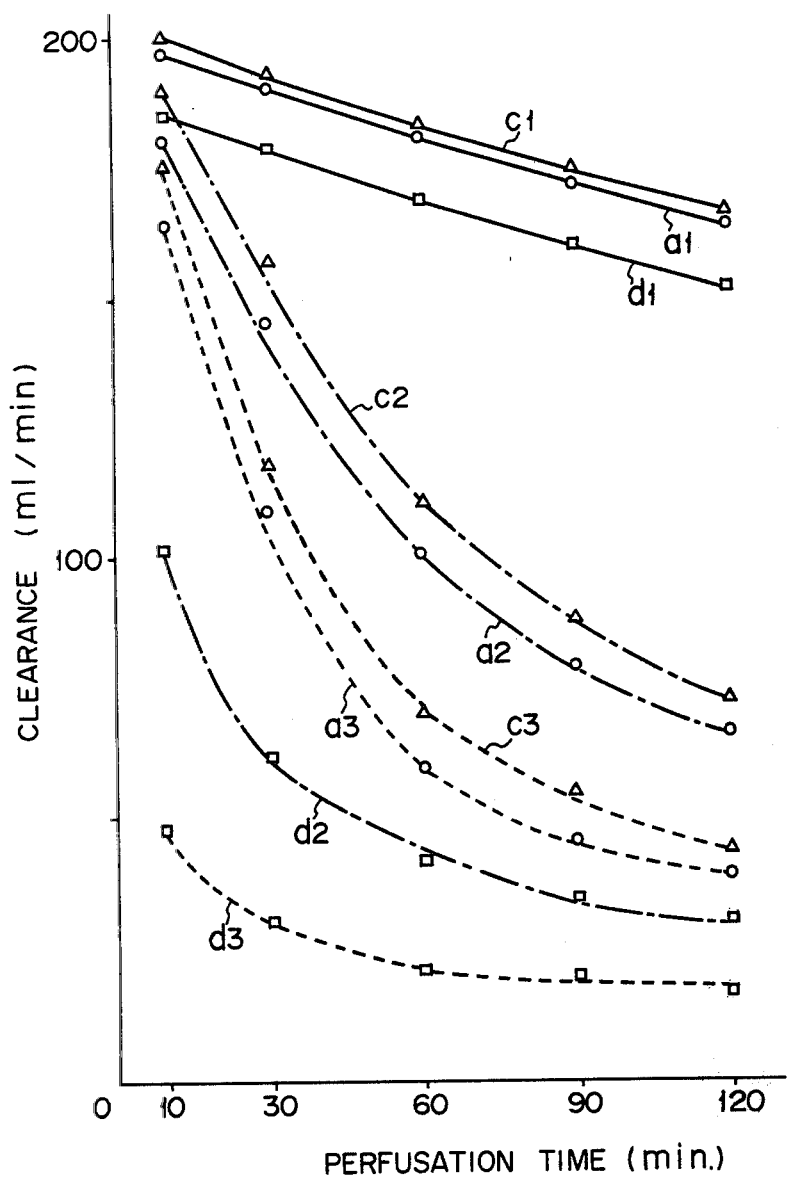

The results are shown in FIG. 10. Referring to this figure, curves a1, a2, and a3 indicate the change in the DHP column for the case of Example 2; curves c1, c2 and c3 indicate the same for the case of Comparative Example 2; and curves d1, d2 and d3 indicate the same for the case of Comparative Example 3. As for the numerals attached to them, numeral 1 denotes the result for creatinine; 2, for vitamin B12; and 3, for inulin.

It is seen from the results shown in FIG. 10 that clearance was high and adsorption ability was not degraded with the DHP column according to the present invention.

Such effects were obtained when the ratio of heparin to activated carbon was in the range of 50 to 5,000 units/g.

What we claim is:

1. An apparatus for detoxifying a body fluid comprising:
    a columnar hollow container having an inlet and an outlet for body fluid; and
    a plurality of noncoated petroleum pitch activated carbon particles;
    said container being filled with (i) said particles and (ii) a physiologically acceptable filling liquid containing between 50 and 5,000 units of heparin per gram of said activated carbon particles; and
    said activated carbon particles having been washed in a physiologically acceptable cleaning solution with ultrasonic waves until the number of carbon dust fine particles released in the cleaning solution is less than 100 particles/ml for particles of more than $2\mu$ particle size and less than 10 particles/ml for particles of more than $5\mu$ particle size.

2. An apparatus according to claim 1, wherein filtering materials having pores small enough to support the activated carbon particles are disposed at the inlet side and the outlet side of the container.

3. An apparatus according to claim 2, wherein the activated carbon has a particle diameter of 0.1 to 1 mm.

4. An apparatus according to claim 2, wherein the filtering materials have pores of 200 to 250μ diameter.

5. An apparatus according to claim 4, wherein the container has a capacity of 50 to 600 cc.

6. An apparatus according to claim 5, wherein said activated carbon particles are filled in the container to maximum density.

7. An apparatus according to claim 1, wherein the filling liquid is water, a physiological saline solution or an aqueous solution of dextran.

8. An apparatus for detoxifying a body fluid comprising a hollow container having an inlet and an outlet for body fluid, noncoated petroleum pitch activated carbon particles filled in the container together with a physiologically acceptable filling liquid containing between 50 and 5,000 units of heparin per gram of said activated carbon particles; and filtering materials disposed at the inlet side and the outlet side of the container to support the activated carbon particles within the container, the apparatus being obtained by (a) washing the activated carbon particles in a physiologically acceptable cleaning solution by means of ultrasonic waves; (b) during the washing, removing carbon dust fine particles released in the cleaning solution from the activated carbon particles until the number of carbon dust fine particles in the cleaning solution is less than 100 particles/ml for particles of more than 2μ particles size and less than 10 particles/ml for particles of more than 5μ particle size, with or without the circulation of the cleaning solution; (c) filling the thus washed carbon particles in the container together with the filling liquid comprising the cleaning solution or a substitute liquid therefore, (d) supporting the filled carbon particles by the filtering materials, (e) sealing the inlet and outlet, and (f) sterilizing the apparatus in an autoclave.

9. An apparatus according to claim 8, wherein the filling liquid is water, a physiological saline solution or an aqueous dextran solution.

* * * * *

UNITED STATES PATENT AND TRADEMARK OFFICE
CERTIFICATE OF CORRECTION

PATENT NO. : 4,358,376
DATED : November 9, 1982
INVENTOR(S) : Yousuke MORIUCHI et al It is certified that error appears in the above–identified patent and that said Letters Patent are hereby corrected as shown below:

Column 2, line 46: delete "the" and replace it with --relative motion causing--.

Signed and Sealed this

Twenty-sixth Day of July 1983.

[SEAL]

Attest:

GERALD J. MOSSINGHOFF

Attesting Officer    Commissioner of Patents and Trademarks